United States Patent [19] [11] 4,219,622
Umezawa et al. [45] Aug. 26, 1980

[54] PROCESS FOR PRODUCING ANTIBIOTICS MA 144-$M_1$ AND MA 144-$M_2$

[75] Inventors: Hamao Umezawa; Tomio Takeuchi, both of Tokyo; Hiroshi Naganawa; Masaaki Ishizuka, both of Denenchohushi; Norio Shibamoto, Chigasakishi; Toshikazu Oki, Kamakurashi; Taiji Inui, Chigasakishi, all of Japan

[73] Assignee: Zaidan Hojin Biseibutsu Kagaku Kenkyu Kai, Tokyo, Japan

[21] Appl. No.: 17,525

[22] Filed: Mar. 5, 1979

Related U.S. Application Data

[62] Division of Ser. No. 879,536, Feb. 21, 1978, which is a division of Ser. No. 780,730, Mar. 24, 1977, Pat. No. 4,144,329.

[30] Foreign Application Priority Data

Apr. 7, 1976 [JP] Japan ................................. 51/39688

[51] Int. Cl.² ........................................... C12P 19/56
[52] U.S. Cl. ..................................... 435/78; 435/886; 435/888; 435/189
[58] Field of Search .......................................... 435/78

[56] References Cited

U.S. PATENT DOCUMENTS

| | | | |
|---|---|---|---|
| 3,864,480 | 2/1975 | Wang et al. | 424/120 |
| 3,988,315 | 10/1976 | Umegawa et al. | 435/78 |
| 4,127,714 | 11/1978 | Umezawa et al. | 435/78 |

FOREIGN PATENT DOCUMENTS 846130 8/1960 United Kingdom .

OTHER PUBLICATIONS

Keller-Schublein et al., Antimicrobial Agents and Chemotherapy, pp. 68–77 (1970).
Chemical Abstracts 54:1466i and 1467a (1960).
J. Antibiotics 28:830 (1975).
Chem. Ber. 92:1904–1909 (1959).
Biochem J. 81:101–104 (1961).
Naturwiss 52:539–540 (1965).
Chemical Abstracts 643896g (1966).
Chemical Abstracts 67:90573z (1967).
J. Bacterial 72:90–94 (1956).
J. Antibiotics 25:393–399 (1972).
Index of Antibiotics from Actinomyces, Umezawa Univ. Park Press, pp. 111, 220, 221, 542 (1967).
Antibiotics, vol. 1, Mechanism of Action Springs Vendag, New York, Inc., pp. 190–210 (1967).
Information Bulletin No. 10, International Center of Information of Antibiotics in Collaboration with WHO 12/1972.
J. Am. Chem. Soc. 86:3592–3594 (1964).
Arch. fur Mikrobiol 31:356–358 (1958).
International Journal of Systematic Bacteriology 22:298 (1972).

*Primary Examiner*—Alvin E. Tanenholtz
*Attorney, Agent, or Firm*—David M. Morse

[57] ABSTRACT

New antitumor agents designated MA 144-$M_1$ and MA 144-$M_2$, which are anthracycline glycosides and inhibit the growth of gram-positive bacteria, e.g. *Staphyococcus aureus*, *Bacillus subtilis* and *Sarcina lutea*, and inhibit the growth of animal tumors such as leukemia L 1210, P 388 and sarcoma 180 are produced by fermentation of MA 144-producing strains of streptomyces and by the chemical or enzymatic conversion of aclacinomycin A or cinerubin A.

10 Claims, 9 Drawing Figures

ULTRAVIOLET AND VISIBLE ABSORPTION SPECTRA OF MA 144-M$_1$

INFRARED ABSORPTION SPECTRUM OF MA144-M₁ IN KBr

INFRARED ABSORPTION SPECTRUM OF MA144-M$_2$ IN KBr

NMR SPECTRUM OF MA144-M₂ (100MHz IN CDCl₃, INTERNAL REFERENCE: TMS)

NMR SPECTRUM OF METHYLATED DISACCARIDE
(100 MHz IN CDCl$_3$, INTERNAL REFERENCE: TMS)

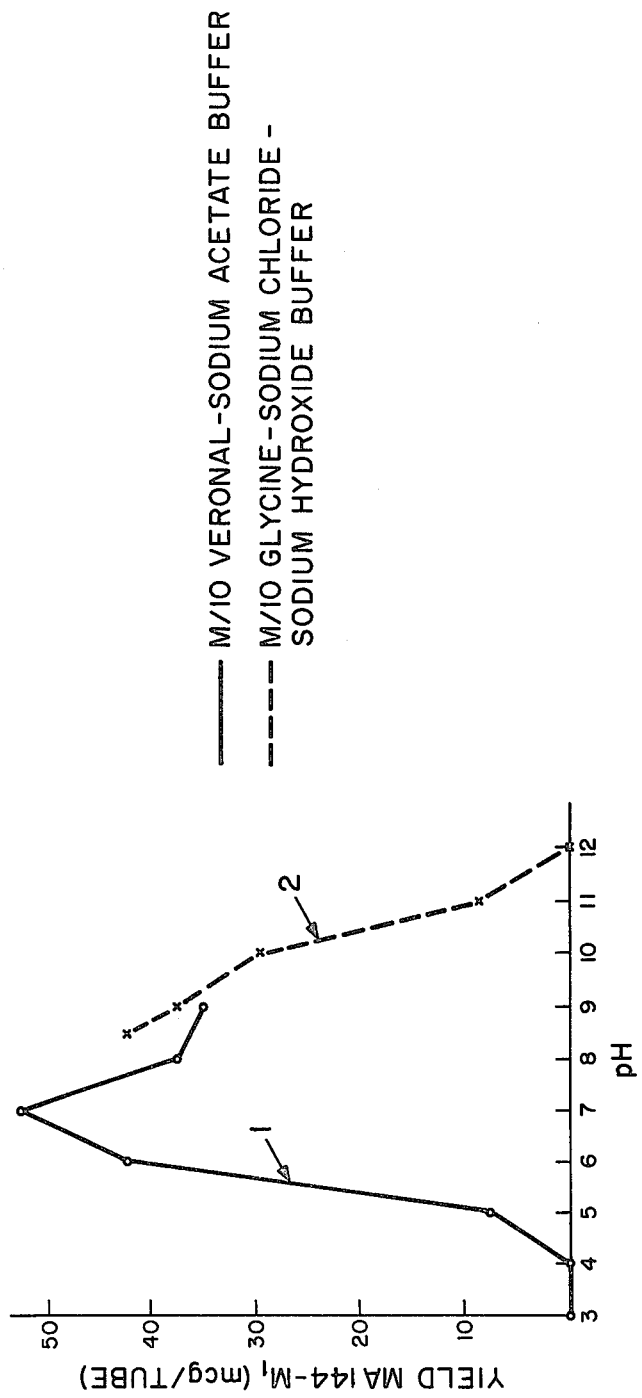

PROCESS FOR PRODUCING ANTIBIOTICS MA 144-M₁ AND MA 144-M₂

CROSS-REFERENCE TO RELATED APPLICATIONS

This application is a division of our prior, co-pending application Ser. No. 879,536 filed Feb. 21, 1978, which in turn is a division of co-pending application Ser. No. 780,730 filed Mar. 24, 1977 now U.S. Pat. No. 4,144,329.

BACKGROUND OF THE INVENTION

1. Field of the Invention

This invention relates to new anthracycline glycoside antitumor antibiotics, to processes for their preparation and to pharmaceutical compositions containing them. More, particularly, it relates to new antitumor antibiotics designated MA 144-$M_1$ and MA 144-$M_2$, to processes for the preparation thereof by the fermentation of MA 144-producing strains belonging to streptomyces and by the chemical or enzymatic conversion of aclacinomycin A or cinerubin A, to methods for their recovery and purification, and to their application as chemotherapeutic agents for the inhibition of malignant tumors and for the treatment of infectious diseases caused by gram-positive bacteria.

2. Description of the Prior Art

A number of anthracycline glycosides have been found in the cultured broth of streptomyces. Among them, daunomycin and adriamycin have already been applied clinically for human cancers. In the continuation of the study of antitumor antibiotics, especially anthracycline glycosides produced by *Streptomyces galilaeus* MA 144-$M_1$, the present inventors discovered new compounds and after purification and characterization based on their physico-chemical properties, they confirmed that the antibiotics now named MA 144-$M_1$ and MA 144-$M_2$ are new compounds which have potent antitumor activity and low toxicity in animals, and they established processes and methods for their preparation and purification.

Aclacinomycin A is disclosed in U.S. Pat. No. 3,988,315 and by Oki et al. in J. Antibiotics 28: 830 (1975).

Cinerubin A and cinerubin B are disclosed in U.K. Pat. No. 846,130, U.S. Pat. No. 3,864,480, Keller-Schierlein et al., "Antimicrobial Agents and Chemotherapy", page 68 (1970), Chemical Abstracts 54: 1466 i (1960) and J. Antibiotics 28: 830 (1975).

Other anthracycline antibiotics having aklavinone or ε-pyrromycinone aglycone moieties are disclosed in the literature as follows:

(a) Pyrromycin: Chem. Ber. 92: 1904–1909 (1959).
(b) Rutilantin: Biochem. J. 81: 101–104 (1961).
(c) Galirubin A and B: Naturwiss. 52: 539–540 (1965). Chemical Abstracts 64: 3896 g (1966). Chemical Abstracts 67: 90573 z (1967).
(d) Aklavin: J. Bacteriol. 72: 90 (1956).
(e) Requinomycin: J. Antibiotics 25: 393 (1972).

For further illustrative and summary disclosures of anthracycline antibiotics, see Index of Antiobiotics from Actinomycetes, Hamao Umezawa, Editor-in-chief, University Park Press, State College, Pa., U.S.A. (1967) as follows:

| Antibiotic | Page Number |
| --- | --- |
| Aklavin | 111 |
| Cinerubin A | 220 |
| Cinerubin B | 221 |
| Pyrromycin | 542 |

The textbook Antibiotics, Volume 1, Mechanisms of Action, edited by David Gottlieb and Paul D. Shaw, Springer-Verlag New York, Inc., N.Y., N.Y. (1967) at pages 190–210 contains a review by A. DiMarco entitled Daunomycin and Related Antibiotics.

Information Bulletin, No. 10, International Center of Information of Antibiotics, in collaboration with WHO, December, 1972, Belgium, reviews anthracyclines and their derivatives.

This specification on page 25 refers to disclosures on amicetin: see J. Am. Chem. Soc. 86: 3592 (1964).

For a description of *Streptomyces galilaeus*, see Arch. fur Mikrobiol. 31: 356 (1958) and International Journal of Systematic Bacteriology 22: 298 (1972).

SUMMARY OF THE INVENTION

There are provided by the present invention the anthracycline glycoside antitumor antibiotics named MA 144-$M_1$ and MA 144-$M_2$. These antibiotics may be produced either by fermentation of MA 144-producing strains belonging to streptomyces or by the chemical or enzymatic conversion of aclacinomycin A or cinerubin A or materials containing them, all of such processes being included in this invention. The enzymatic conversion can be carried out with use of various types of active enzymes, and the chemical conversion can be carried out in the presence of various reducing agents. MA 144-$M_1$ and MA 144-$M_2$ thus produced can be isolated and purified by conventional methods used to isolate and purify water-insoluble antibiotics, said methods including at least one process selected from the group consisting of solvent extraction, solvent precipitation, concentration, gel filtration, counter current distribution, chelation with metal ions and adsorption followed by elution from an ion exchange resin, adsorbent siliceous earth material or synthetic adsorbent.

This invention also embraces MA 144-$M_1$ and MA 144-$M_2$ as crude solids, as purified solids, as their salts and as DNA complexes, and the process of preparing the above in which the solution containing MA 144 is freeze-dried after the addition of at least one substance selected from the group consisting of deoxy-ribonucleic acid, glycerol, sugars, amino acids and inorganic or organic acids.

The present invention thus provides the antitumor antibiotics MA 144-$M_1$ and MA 144-$M_2$ which (a) have antimicrobial activities against gram-positive bacteria, (b) are effective in inhibiting the growth of solid and ascitic forms of malignant tumors in mammals, and (c) have a high cytotoxicity and thus inhibit the growth of mammalian tumor cells in culture.

Physico-chemical properties of MA 144-$M_1$ and MA 144-$M_2$ $M_2$ are as follows:

MA 144-$M_1$

Yellow powder with m.p. 149°–150° C.
Empirical formula: $C_{42}H_{55}O_{15}N$
Ultraviolet and visible absorption maxima at 229(775), 258(335), 290(128), 432(155) nm in methanol, 229(815), 259(345), 290(130), 432(160) nm in 0.01 N HCl-methanol and 237(575), 250s(405), 290(125), 323s(80), 526(135) nm in 0.01 N NaOH-methanol.

MA 144-M$_2$

Red needle crystals with m.p. 151°–152° C.

Empirical formula: $C_{42}H_{55}O_{16}N$

Ultraviolet and visible absorption maxima at: 235(600), 259(310), 269(170), 291(105), 492(165) nm in methanol, 235(615), 259(325), 269(185), 291(115), 492(170) nm in 0.01 N HCl-methanol, and 237(505), 269(145), 292(95), 330(55), 554 (175), 597(145) nm in 0.01 N NaOH-methanol.

MA 144-M$_1$ MA 144-M$_2$ are soluble in acidic water, dimethyl sulfoxide, methylcellosolve, methanol, ethanol, ethyl acetate, acetone, chloroform, benzene, toluene, slightly soluble in water, diethyl ether, n-hexane, give a negative ninhydrin reaction and do not reduce Fehling solution.

The present invention also provides pharmaceutical compositions for treatment of infections due to gram-positive microorganisms. Furthermore, the present invention provides pharmaceutical compositions for inhibition of malignant tumors of mammals.

DESCRIPTION OF THE DRAWINGS

FIG. 9 shows the pH curve of the enzyme reaction for formation of MA 144-M$_1$ and MA 144-M$_2$.

DETAILED DESCRIPTION

Figure 1:
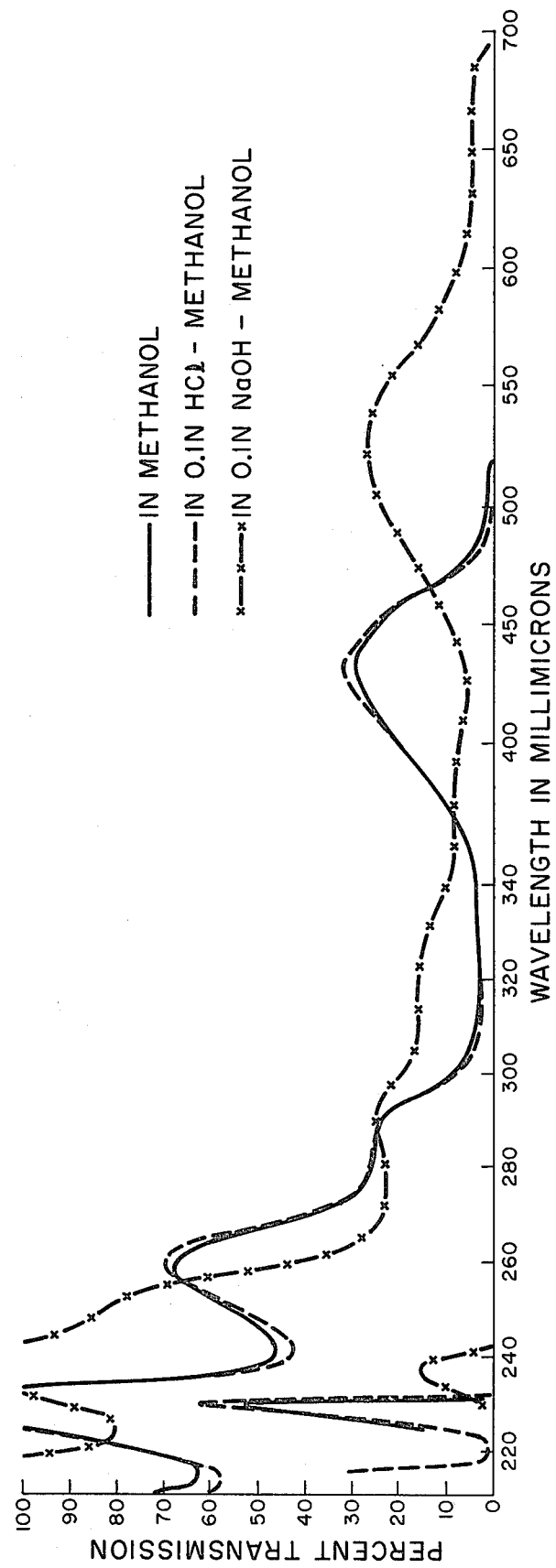
FIG. 1 shows the ultraviolet and visible light absorption spectra of MA 144-M$_1$ in methanol.

The present invention provides two new anthracycline antibiotics, MA 144-M$_1$ and MA 144-M$_2$, which have been found to possess both antimicrobial and antitumor activity. More particularly, the compounds of the present invention exhibit activity against gram-positive bacteria, inhibit the growth of various mammalian tumors such as leukemia L1210 and P388 in mice and possess low toxicity. Accordingly, the compounds are useful as antibacterial agents and antitumor agents.

As used herein, the term MA 144 refers to the antibiotic which includes at least one antibiotic selected from MA 144-M$_1$ and MA 144-M$_2$.

The compounds of the present invention may be produced either by a fermentation process or by the chemical or enzymatic reduction of certain known anthracycline starting materials.

According to one method of preparation, aclacinomycin A, cinerubin A, or a mixture thereof, is enzymatically converted to MA 144-M$_1$, MA 144-M$_2$, or a mixture thereof. The starting material anthracyclines may be used in purified form, as salts or in impure form, e.g. in the form of materials containing the anthracycline substrates such as fermentation broths or crude extracts from such broths.

The enzymatic conversion can be more readily seen from the following reaction scheme:

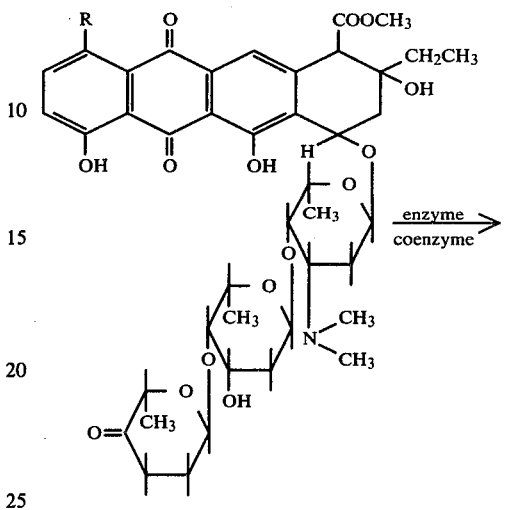

R = H (aclacinomycin A)
R = OH (cinerubin A)

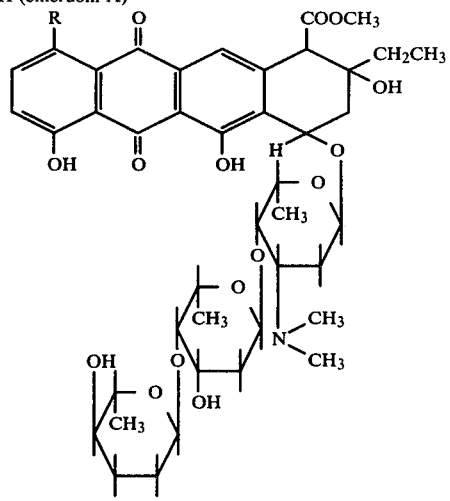

R = H (MA 144-M$_1$)
R = OH (MA 144-M$_2$).

The enzyme system used to reduce the keto group of the cinerulose A sugar moiety may be obtained from certain microorganisms belonging to the genus streptomyces and from various mammalian tissues, e.g. tissues from monkeys, dogs, rabbits, hamsters, rats or mice. In the case of the enzyme obtained from microorganisms, strains belonging to streptomyces which are capable of producing MA 144-M$_1$ and MA 144-M$_2$ and which will be more extensively described below can also be employed in the form of the cultured broth, cell suspension, dried cells, cell homogenate, supernatant solution, partially purified enzyme and immobilized enzyme obtained therefrom. In the case of the enzyme obtained from mammals, various mammalian enzyme sources such as various organs, tissue slices, tissue homogenates, their dried preparations and partially purified enzyme solutions obtained by salting out, organic solvent precipitation, gel filtration and chromatography can also be used. Immobilized enzymes obtained from such mammalian sources are also suitable in this process. A most preferred mammalian source of the converting enzyme system is liver homogenate, e.g. rat liver homogenate.

The conversion reaction from aclacinomycin A to MA 144-$M_1$ or from cinerubin A to MA 144-$M_2$ is carried out by the enzyme system which is obtained from the above mentioned enzyme sources.

The conditions of the enzyme reaction such as pH, temperature, substrate concentration, reaction period, coenzyme, etc. depend upon the state of the enzyme, starting material used, etc. Generally speaking, it is preferable to select the conditions which accelerate the enzyme reaction and which do not inactivate the enzyme system. In general, temperatures from 20° to 42° C., pH from 5.5 to 10.5, a substrate concentration under 5% and a reaction period from 20 to 120 min. are preferable.

The enzyme activity in various sources used in the present invention and the coenzyme requirement for the enzyme activity in rats are shown as follows:

Table 1

| Comparison of enzyme activity in the liver homogenate from various mammals | |
|---|---|
| Mammals | MA 144-$M_1$ formed ($\mu$ moles/g-tissue) |
| Guinea pig | 0.08 |
| Hamster | 0.24 |
| Monkey | 0.38 |
| Mouse | 0.38 |
| Rabbit | 0.26 |
| Rat | 0.37 |

Composition of the enzyme reaction mixture
Liver homogenate (enzyme): 0.8 ml.
NADP solution (2 $\mu$g./ml.): 0.1 ml.
Substrate: aclacinomycin A (800 $\mu$g./ml.) 0.1 ml.
in which NADP is nicotinamide-adenine dinucleotide phosphate, and the reaction was carried out for 1 hr. at 37° C. Determination was carried out by using Shimazu Dual-wave chromato-scanner after extraction of the product with the solvent. (chloroform:methanol=1:1)

Table 2

| Coenzyme requirement for the enzyme reaction (rat liver) | |
|---|---|
| Coenzyme | MA 144-$M_1$ formed ($\mu$moles/g tissue) |
| None | 0 |
| NAD | 0 |
| NADH | 0 |
| NADP | 0.35 |
| NADPH | 0.37 |

The enzyme reaction was carried out according to the method given in Table 1. NAD is nicotinamide adenine dinucleotide, NADH is the reduced form of NAD, NADP is the same as in Table 1, and NADPH is the reduced form of NADP.

FIG. 9 shows the optimal pH in the enzymatic formation of MA 144-$M_1$ by rat liver homogenate, in which the vertical line shows $\mu$g./tube of MA 144-$M_1$ formed, and the buffer solution used to adjust pH is M/10 veronal-sodium acetate in solid line 1 and M/10 glycine-sodium chloride-sodium hydroxide in dotted line 2.

The compounds of the present invention may also be prepared by chemical reduction of aclacinomycin A and/or cinerubin A with various reducing agents capable of selectively reducing the cinerulose A sugar moiety to the amicetose sugar moiety of MA 144-$M_1$ and MA 144-$M_2$. Preferred reducing agents are the metal hydrides such as sodium borohydride, lithium hydrides (e.g. LiH, LiAlH$_4$) and aluminum hydrides (e.g. AlH$_3$).

The chemical reduction reaction in the present invention can be carried out either in a single solvent system or a mixed solvent system which dissolves the antibiotics according to the present invention. The reaction conditions such as temperature, substrate concentration, reaction period, etc. depend upon the solvent system, starting material and the like, with conditions achieving the highest yield and reaction rate preferably chosen.

Other than the chemical and enzymatic processes mentioned above, the MA 144 antibiotics can also be produced fermentatively by cultivating the MA 144-producing strains mentioned hereinafter under suitable conditions. For fermentative production of the antibiotics according to the present invention, MA 144-producing strains belonging to the genus Streptomyces can be used such as *Streptomyces galiaeus* MA 144-$M_1$ ATCC 31133 (FERM P-2455), Streptomyces sp. ME 505-HE1 ATCC 31273 (FERM P-3667), *S. galilaeus* ATCC 14969, *S. cinereoruber* ATCC 19740, *S. niveoruber* ATCC 14971, *S. antibioticus* ATCC 8663, *S. purpurascens* ATCC 25489 and mutants thereof. Among the above-mentioned strains, *St. galilaeus* MA 144-$M_1$ ATCC 31133 (FERM P-2455) was isolated by the present inventors from a soil sample collected at Osaki, Shinagawa-ku, Tokyo, Japan. A culture of *St. galilaeus* MA 144-$M_1$ was deposited in the American Type Culture Collection, Rockville, Maryland and in the Fermentation Research Institute, Japan, and was added to their permanent collections of microorganisms as ATCC No. 31133 and FERM No. 2455, respectively.

The strain No. MA 144-$M_1$ has the following properties:

(1) Morphological properties:

Under a microscope, open spirals well developed from branched substrate mycelia are observed. There are no whorls, and the mature spore chain is moderately long with more than ten spores. The spores are ellipsoidal and measure 0.4 to 0.8$\mu$×0.8 to 1.6$\mu$ and their surface is smooth.

(2) Properties on various media:

The description in parenthesis follows the color standard of the "Color Harmony Manual" published by Container Corporation of America, U.S.A.

(a) On glucose-aspargine agar, incubated at 27° C.: light yellowish brown growth (3gc, Lt. Tan); no aerial mycelium; no soluble pigment.

(b) On sucrose-aspargine agar, incubated at 27° C.: colorless or light yellowish brown growth (3gc, Lt. Tan); no aerial mycelium; no soluble pigment.

(c) On glycerol-aspargine agar (ISP medium No. 5), incubated at 27° C.: yellowish orange (4ic, Suntan) to brown (51 g., Cocoa Brown) growth; white to light gray (2fe, Covert Gray) aerial mycelium; brown soluble pigment.

(d) On starch-inorganic salts agar (ISP medium No. 4), incubated at 27° C.: Pale orange (3ea, Lt. Melon Yellow) to pale yellowish brown (3ie, Camel) growth; light gray (2fe, Covert Gray) to gray (e, Gray) aeriel mycelium; brown soluble pigment.

(e) On tyrosine agar (ISP medium No. 7), incubated at 27° C.: Brownish gray (3li, Beaver) to brown (4lg, Toast Tan) aerial mycelium, black soluble pigment.
(f) On nutrient agar, incubated at 27° C.: Colorless to grayish brown growth; no aerial mycelium, brown soluble pigment.
(g) On yeast extract-malt extract agar (ISP medium No. 2), incubated at 27° C.: Light brown (4le, Maple) to brown (4ng, Lt. Brown) growth; light gray (3fe, Silver Gray) to gray (3ih, Beige Gray) aerial mycelium; brown soluble pigment.
(h) On oatmeal agar (ISP medium No. 3), incubated at 27° C.: colorless to pale yellowish brown (2gc, Bamboo) growth; light gray (3fe, Silver Gray) aerial mycelium; brown soluble pigment.
(i) On glycerol-nitrate agar, incubated at 27° C.: Colorless to pale yellowish brown (3gc, Lt. Tan) or light olive gray (2db, parchment) growth; no aerial mycelium; no soluble pigment.
(j) On starch agar, incubated at 27° C.: Pale yellowish brown (3gc, Lt. Tan) growth; gray (e, Gray) aerial mycelium; slight brown soluble pigment.
(k) On calcium malate agar, incubated at 27° C.: Colorless growth; grayish white (b, Oyster white) to light brownish gray (3dc, Natural) aerial mycelium; no soluble pigment.
(l) On gelatin stab, incubated at 20° C.: Pale brown to pale yellowish brown growth; white aerial mycelium; brown soluble pigment.
(m) On glucose-peptone-gelatin stab, incubated at 27° C.: Pale brown to brown growth; no aerial mycelium; brown soluble pigment.
(n) On skimmed milk, incubated at 37° C.: Pale brown to brown growth; no aerial mycelium; brown soluble pigment.

(3) Physiological properties:
(a) Growth temperature was examined on maltose-yeast extract agar (maltose 1.0%, yeast extract 0.4%, agar 3.5%, pH 6.0) at 20°, 24°, 27°, 30°, 37° and 50° C. Optimal temperature for the growth is 27° C. to 37° C. with no growth at 50° C.
(b) Gelatin liquefaction on 15% gelatin stab at 20° C.: and on glucose-peptone-gelatin stab at 27° C.: On the former medium, gelatin liquefaction was observed as weak with 14 days incubation, but as weak or moderate after 7 days incubation on the latter medium.
(c) Starch hydrolysis on starch-inorganic salts agar at 27° C.: Weak hydrolysis was observed after 5 days incubation.
(d) Peptonization and coagulation of skimmed milk at 37° C.: Moderate to strong peptonization began after 5 days incubation and finished after around 17 days. No coagulation.
(e) Melanin formation on tyrosine agar (ISP medium No. 7), tyrosine-yeast extract broth (ISP medium No. 1) and peptone-yeast extract-ferrous agar (ISP medium No. 6) at 27° C.: positive on all media.
(f) Liquefaction of calcium malate on calcium malate agar at 27° C.: Strongly positive.
(g) Nitrate reduction on peptone agar containing 1.0% sodium nitrate (ISP medium No. 8) at 27° C.: Positive.
(h) Utilization of carbohydrates of Pridham-Gottlieb basal medium (ISP medium No. 9), incubated at 27° C.: Abundant growth with L-arabinose, D-xylose, glucose, D-fructose, sucrose, inositol, L-rhamnose and raffinose; no growth with D-mannitol.

Summarizing the above characteristics of No. MA 144-$M_1$, the strain belongs to the genus Streptomyces and chromogenic type, and produces brown soluble pigment on various agar media. Aerial mycelium forms open spirals, but no whorls. The spore surface is smooth. The growth on various media is found to be pale yellowish brown to brown in general, but olive in a few media, and aerial mycelium is light gray. Nitrate is reduced to nitrite. Proteolytic action is weak to moderate and starch hydrolysis is relatively weak. Melanin is produced on tyrosine agar, tyrosine-yeast extract broth and peptone-yeast extract-ferrous agar.

Among known species of Streptomyces, strain No. MA 144-$M_1$ resembles *Streptomyces galilaeus*. Reference 1: Archiv fur Microbiologie 31: 356, (1958). Reference 2: International Journal of Systematic Bacteriology 22: 298, (1972). With particular attention to differentiation based on the morphology, color of the aerial mycelium and other physiological properties, the difference between the present strain and the standard strain of *S. galilaeus* ISP 5481 obtained was investigated by parallel cultures.

From the results, the present strain agrees very closely with *S. galilaeus* ISP 5481 in morphology and color of the growth and mycelium on various media and physiological properties. Furthermore, similarity of both strains exists in the fermentation products; that is, cinerubin which can be produced by *S. galilaeus* is one of the by-products of the present strain. Thus, strain No. MA 144-$M_1$ can be identified as *Streptomyces galilaeus*.

The strain Streptomyces sp. ME 505-HE1 FERM P-3667 was also isolated from a soil sample collected at Osaki, Shinagawa-ku, Tokyo, Japan and was deposited in the Fermentation Research Institute, Japan and American Type Culture Collection and added to their permanent collections of microorganisms as FERM P-3667 and ATCC 31273, respectively. Brief descriptions of its morphological and physiological properties are as follows:

Characteristics of Streptomyces sp. ME 505-HE1 are under investigation in detail. The strain No. ME 505-HE1 has the following characteristics at present: Under the microscope, the aerial mycelia do not have verticillate branch and spiral structure. The growth on the various media is found to be colorless, pale reddish brown to dark brownish purple, and aerial mycelium is not formed or formed slightly with white to pinkish white. Dull red soluble pigment are slightly formed. Melanine formation is positive. Thus, the strain No. 505-HE1 belongs to the genus Streptomyces.

Other than the above mentioned newly isolated strains, other known streptomyces such as *S. galilaeus* ATCC 14969, *S. cinereoruber* ATCC 19740, *S. niveoruber* ATCC 14971, *S. antibioticus* ATCC 8663, *S. purpurascens* ATCC 25489 and mutants thereof also can be used in the present invention.

Since the Streptomyces are easily mutatable naturally or artificially, *S. galilaeus* No. MA 144-$M_1$ and other microorganisms in the present invention include the typical strain described above and all natural and artificial variants and mutants thereof. It is especially desired and intended to comprise MA 144-producing mutants produced from the abovementioned strains by known methods.

As to the fermentative production of the MA 144-$M_1$ and MA 144-$M_2$, a submerged aerobic culture is especially advantageous for the production of large quantities of the antibiotics. Media consisting of known kinds of nutritional sources for antinomycetes are useful, and the general procedures used for the cultivation of other antinomycetes are applicable to the cultivation according to this invention. The medium preferably contains commercially available products such as glycerol, glucose, starch, dextrin, maltose, molasses, oils, fats, lipids and the like as carbon sources in either purified or crude state, commercially available products such as soybean meal, malt extract, pentone, yeast extract, distiller's solubles, fish meal, gluten meal, corn steep liquor, cottonseed flour, casein, hydrolyzed protein substances, nitrates, ammonium salts, urea and the like as the nitrogen sources, inorganic salts such as sodium chloride, potassium chloride, potassium phosphate, magnesium sulfate, calcium carbonate and trace amounts of heavy metal salts such as copper, zinc, manganese, iron, and the like. In the aerated submerged culture, an antifoamer such as liquid paraffin, soybean oil, fat or silicone is used. Any fermentation temperature can be employed within the range of 20° C. to 35° C., in which an MA 144-producing organism can grow, although the preferred range of temperature is from 25° C. to 30° C. The pH of the culture medium ranges from 5 to 8.0. The period necessary for the production is usually 48 to 72 hours.

To isolate MA 144-$M_1$ or MA 144-$M_2$ from the reaction mixture or the cultured broth, the following procedure is provided as an example:

After completion of the enzyme reaction, MA 144-$M_1$ or MA 144-$M_2$ in the reaction mixture is extracted with water-immiscible organic solvents such as ethyl acetate, butyl acetate, chloroform, benzene, n-butanol, methyl propyl ketone, methylene chloride, toluene etc., in a neutral to weak acidic state. Instead of or in combination with the solvent extraction of the reaction mixture, chromatography using active carbon, alumina, silica gel, Sephadex LH-20 (Trademark, Pharmacia Fine Chemicals AB) etc. and countercurrent distribution using a suitable solvent system offer more convenient procedure for the recovery and purification of MA 144-$M_1$ or MA 144-$M_2$. Solvent extracts containing the said compound are re-extracted directly or after concentration under reduced pressure with water-immiscible organic solvents, and the solvent layer including MA 144-$M_1$ or MA 144-$M_2$ is mixed with acidic water with its pH under 3.0, then MA 144-$M_1$ or MA 144-$M_2$ transferred to an acidic aqueous layer is reextracted with suitable organic solvents. The active substance is obtained as a crude pigmented powder by concentration under reduced pressure to dryness from the organic solution. By repeating the said procedures, the compounds can be obtained in purified form.

After adding water to the chemical reaction mixture, MA 144-$M_1$ or MA 144-$M_2$ is extracted, purified and obtained as a crude powder according to the above-mentioned procedures. The solution containing the MA 144-$M_1$ or MA 144-$M_2$ can also be lyophilized alone or with at least one substance selected from serum, serum albumin, globulin, gelatin, glycerol, sugars, amino acids, deoxyribonucleic acid and organic or inorganic acids such as hydrochloric acid, phosphoric acid, sulfuric acid, acetic acid, propionic acid, oleic acid, palmitic acid, citric acid, succinic acid and pantothenic acid. MA 144-$M_1$ or MA 144-$M_2$ in the fermentation broth is obtained by the same purification procedures as mentioned for the enzyme reaction mixture.

In order to obtain pure MA 144-$M_1$ or MA 144-$M_2$, further purification can be carried out by column chromatography using various adsorbents such as silicic acid, alumina, Sephadex LH-20 (Trademark, Pharmacia Fine Chemicals AB) ion-exchangers such as weakly acidic resins and Amberlite XAD (Trademark, Rohm and Haas Co., Inc.), and active carbon, gel filtration, and chelation with various metals, and the combination with at least one or more processes selected from the methods of chelation with metal ions, solvent precipitation, solvent extraction, countercurrent distribution, chromatography, concentration, adsorption to the adsorbent, and adsorption followed by elution from an ion exchange resin, an adsorbent siliceous earth or a synthetic adsorbent in a conventional way which will be mentioned in detail in the examples.

The following are physicochemical properties of pure MA 144-$M_1$ and MA 144-$M_2$:

MA 144-$M_1$

Weakly basic, lipophilic and yellow powder. Elemental analysis yields the following values:

| Found | | Calcd. | |
|---|---|---|---|
| C = | 62.37 | C = | 61.98 |
| H = | 7.08 | H = | 6.81 |
| O = | 28.81 | O = | 29.49 |
| N = | 2.07 | N = | 1.72 |
| | | | for $C_{42}H_{55}O_{15}N$ |

Molecular weight = 814

The melting point and specific rotation ($[\alpha]_D^{20}$ of its 1% solution in chloroform) exhibit 149° to 150° and +40°, respectively. Its absorption spectra in the ultraviolet and in the visible range in methanol show maxima at the following wave-lengths (FIG. 1):

| | $\lambda_{max}(E^{1\%}_{1\ cm})$ |
|---|---|
| in MeOH | 229(775), 258(335), 290(128), 432(155) |
| in 0.01N HCl—MeOH | 229(815), 259(345), 290(130), 432(160) |
| in 0.01N NaOH—MeOH | 237(575), 250$_s$(405), 290(125), 323$_s$(80), 526(135) | s: shoulder

Figure 2:
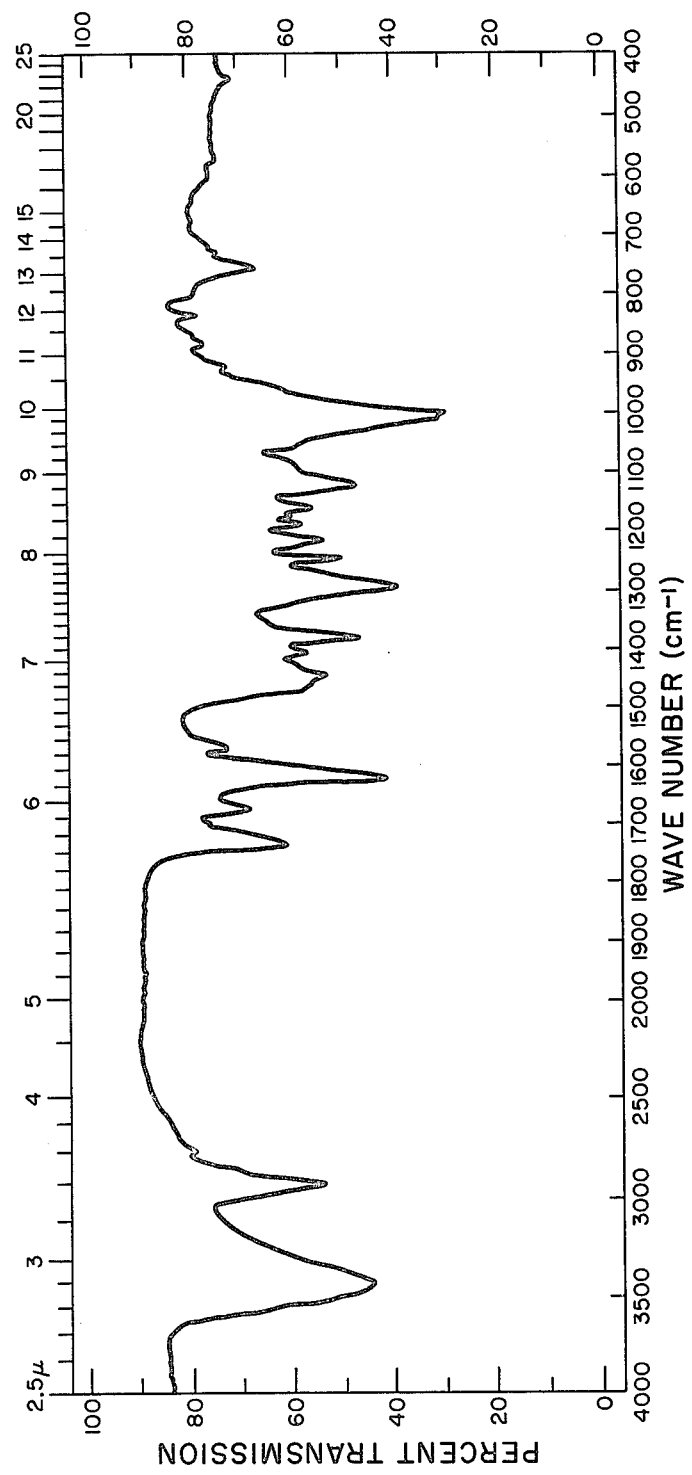
FIG. 2 shows the infrared absorption spectrum of MA 144-M$_1$ in potassium bromide.
Figure 3:
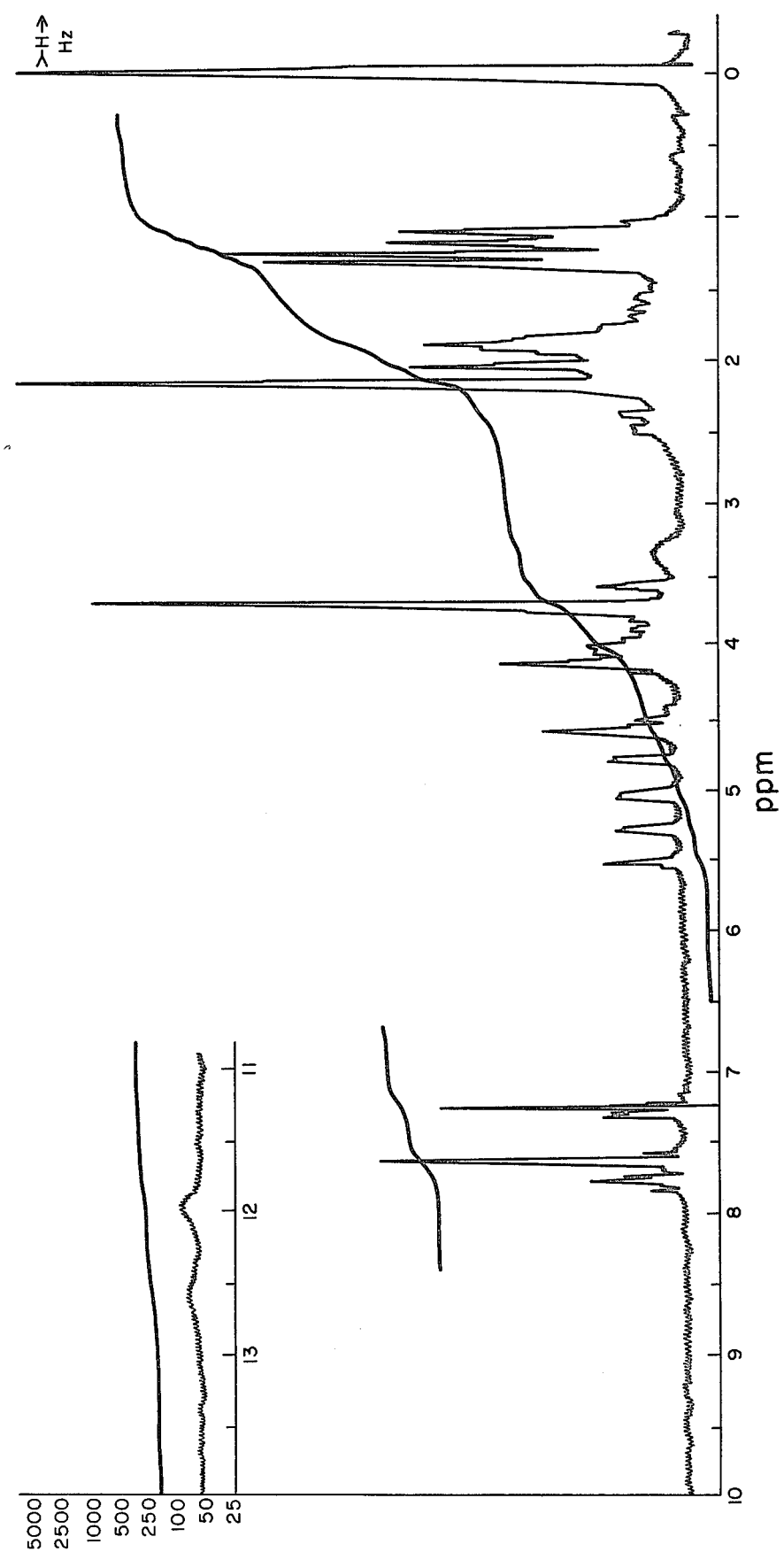
FIG. 3 shows the NMR spectrum of MA 144-M$_1$ in CDCl$_3$(100 MH$_z$).

In FIG. 1, the solid line shows the ultraviolet and visible light absorption spectra in methanol, the dotted line is that in 0.01 N HCl-methanol, and the x—x—x line is that in 0.01 N NaOH-methanol. FIG. 2 shows the infrared absorption spectrum (KBr tablet). FIG. 3 shows the nuclear magnetic resonance spectrum (100 MHz, CDCl$_3$).

MA 144-$M_1$ is soluble in acidic water, dimethyl sulfoxide, methylcellosolve, methanol, ethanol, ethyl acetate, acetone, chloroform, benzene, toluene and slightly soluble in water, diethyl ether and n-hexane. On the other hand, the hydrochloride salt is soluble in water, methanol and chloroform, but slightly soluble in acetone and ethyl acetate. The methanol solution of MA 144-$M_1$ is yellow in conc. HCl, but turns to reddish brown in concentrated sulfuric acid. With alcoholic magnesium acetate, the solution shows a red color and turns to reddish purple on alkalinization. MA 144-$M_1$ gives a negative ninhydrin reaction and does not reduce Fehling solution.

MA 144-$M_2$

Weakly basic, lipophilic and red needle crystals. Elemental analysis yields the following values:

| Found | C = 60.43 | Calcd. | C = 60.79 |
|---|---|---|---|
| | H = 6.74 | | H = 6.68 |
| | O = 29.70 | | O = 30.84 |
| | N = 1.75 | | N = 1.69 |
| | | | for $C_{42}H_{55}O_{16}N$ |

Molecular weight = 830

The melting point is 151° to 152° C. and the specific-rotation ($[\alpha]_D^{20}$ of 1% solution in chloroform) exhibits +127°. The absorption spectra in the ultraviolet and in the visible ranges show maxima at the following wavelengths (FIG. 4):

| | $\lambda_{max}(E^1_{1cm})$ |
|---|---|
| in MeOH | 235(600), 259(310), 269(170), 291(105), 492(165). |
| in 0.01N HCl—MeOH | 235(615), 259(325), 269(185), 291(115), 492(170). |
| in 0.01N NaOH—MeOH | 237(505), 269(145), 292(95), 330 (55), 554(175), 597(145). |

Figure 4:
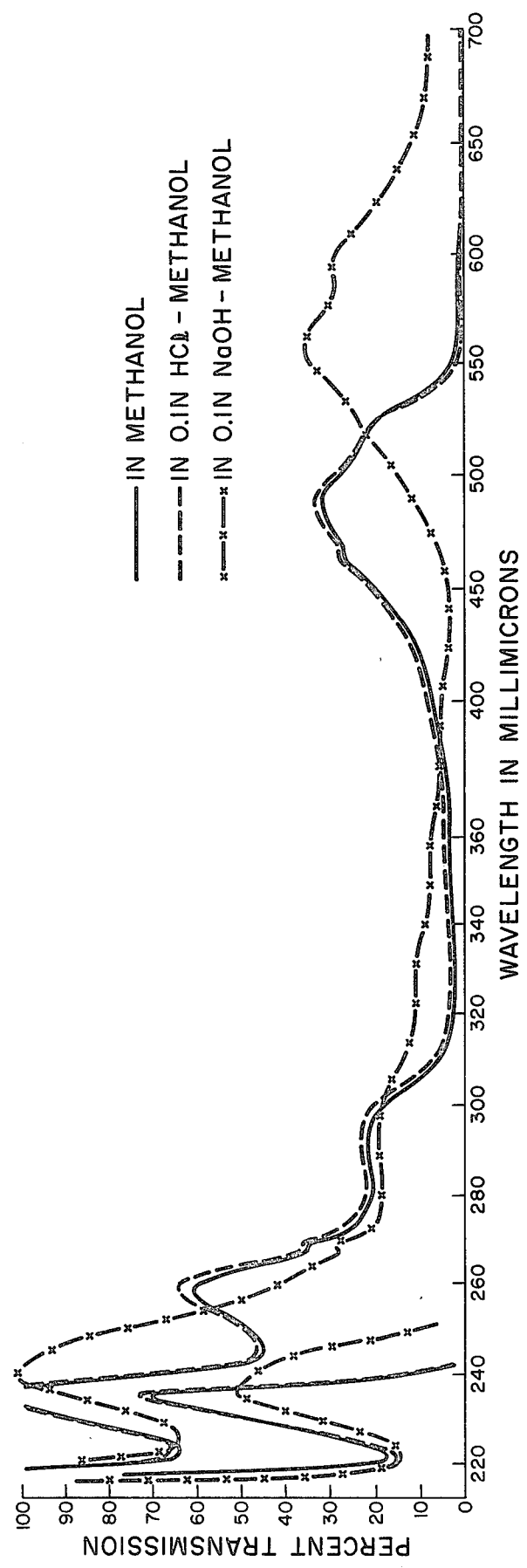
FIG. 4 is the ultraviolet and visible light absorption spectra of MA 144-M$_2$ in methanol.

In FIG. 4, the solid line shows the ultraviolet and visible light absorption spectra in methanol, the dotted line is that in 0.01 N HCl-methanol, and the x—x—x line is that in 0.01 N NaOH-methanol.

Figure 5:
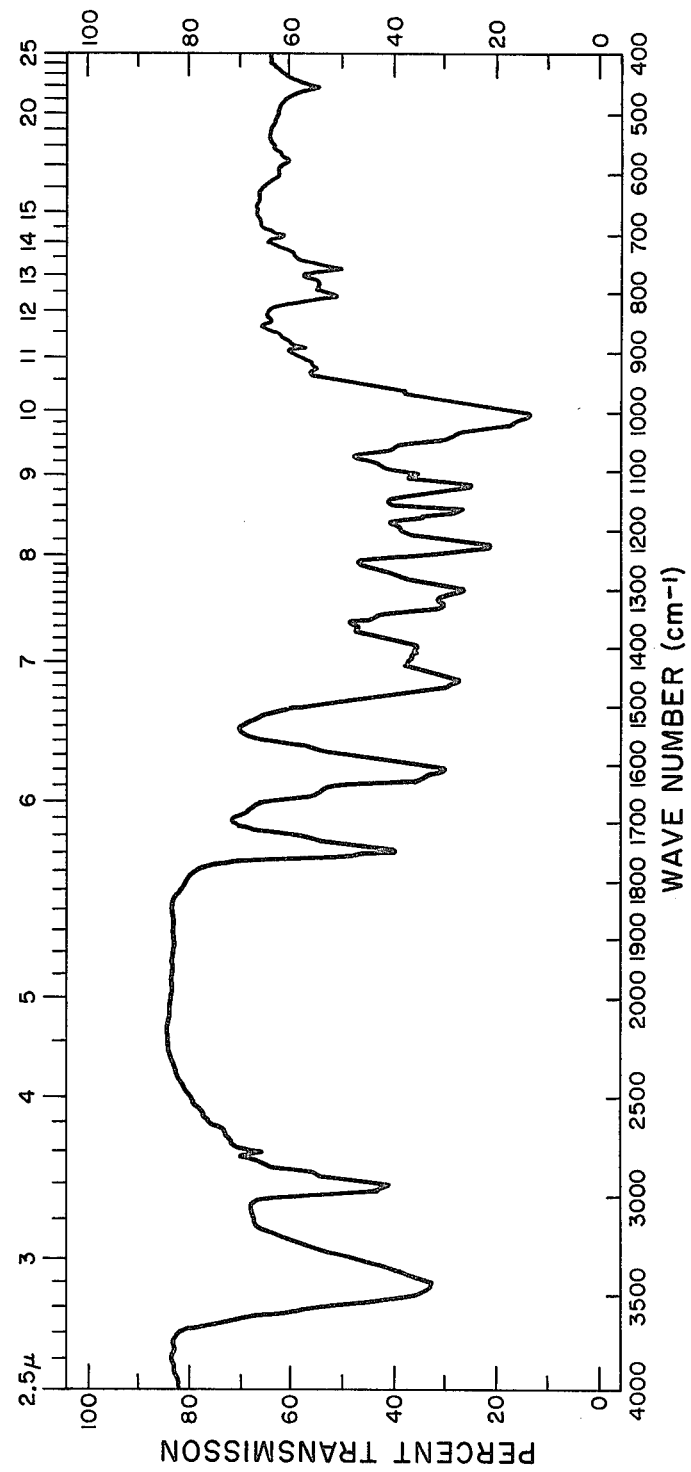
FIG. 5 is the infrared absorption spectrum of MA 144-M$_2$ in potassium bromide.
Figure 6:
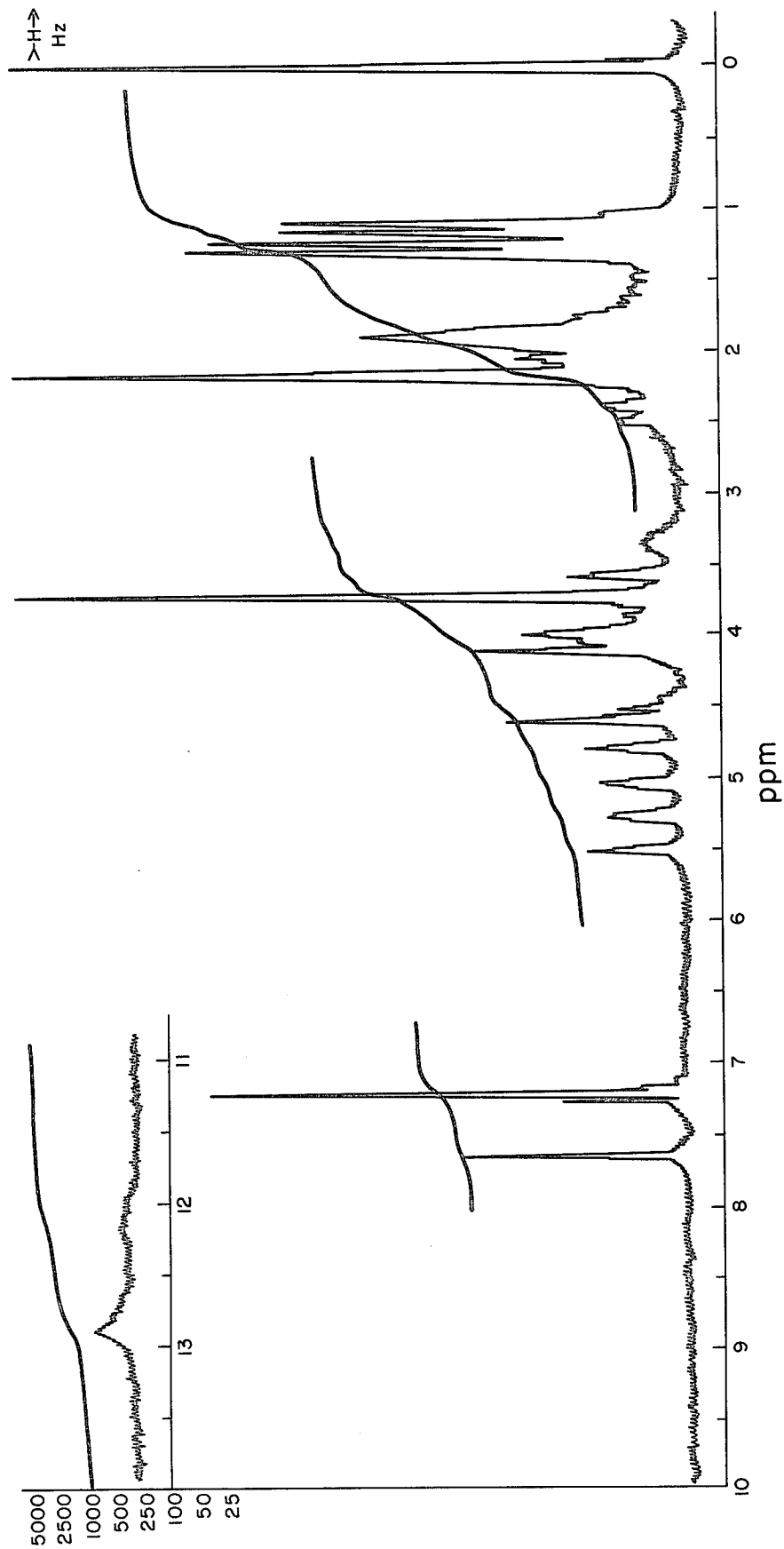
FIG. 6 shows the NMR spectrum of MA 144-M$_2$ in CDCl$_3$(100 MH$_z$).

FIG. 5 shows the infrared absorption spectrum (KBr tablet) and FIG. 6 shows the nuclear magnetic resonance spectrum (100 MHz, CDCl$_3$).

MA 144-M$_2$ is soluble in acidic water, dimethyl sulfoxide, methyl cellosolve, chloroform, ethyl acetate, methanol, ethanol, acetone, benzene, and slightly soluble in water, n-hexane, cyclohexane, diethyl ether and petroleum ether. The hydrochloride salt is soluble in water, methanol, ethanol and chloroform, but slightly soluble in acetone and ethyl acetate. MA 144-M$_2$ gives a negative ninhydrin reaction and does not reduce Fehling solution.

The methanol solution is red in concentrated hydrochloric acid and turns to violet in concentrated sulfuric acid. The solution appears reddish purple in alcoholic magnesium acetate, and gives purplish blue in NaOH solution.

The chemical structure of the said compounds, MA 144-M$_1$ and MA 144-M$_2$, was determined as follows:

On hydrolysis of MA 144-M$_1$ or MA 144-M$_2$ with dilute hydrochloric acid, physicochemical properties such as the absorption spectra of ultraviolet, visible and infrared ranges, mass and nuclear magnetic resonance, melting point, elementary analysis and Rf values on silicic acid thin layer of the aglycone part obtained coincided fully with those of the aglycone obtained from the starting material, that is, the aglycone of MA 144-M$_1$ was aklavinone and that of MA 144-M$_2$ was ε-pyrromycinone.

On the other hand, comparing the Rf values on silicic acid thin-layer of the sugar moieties obtained by hydrolysis from the starting material (aclacinomycin A or cinerubin A) with those of the compounds in the present invention, rhodosamine and 2-deoxyfucose were detected in both, but the terminal sugar, i.e. L-cinerulose, was different. Furthermore, the methylated disaccharide, which was obtained from MA 144-M$_1$ and MA 144-M$_2$ by partial methanolysis in methanol containing 0.1 N hydrochloric acid at room temperature, was extracted with ether, purified by silicic acid and Sephdex LH-20 (Trademark) column chromatography, and then crystallized as white plate crystals in ether.

Physicochemical properties of the said methylated disaccharide are as follows:

| Elemental analysis | | | |
|---|---|---|---|
| | % | | % |
| Found | C = 57.09 | Calcd. | C = 56.51 |
| | H = 8.61 | | H = 8.75 |
| | O = 34.30 | | O = 34.74 |
| | | for $C_{13}H_{24}O_6$ | |

Molecular weight = 276
Melting point: 87 to 91° C. (sublimation point)
Specific rotation: $[\alpha]_D^{20}$ = −161° (c = 1.0, chloroform)

Figure 7:
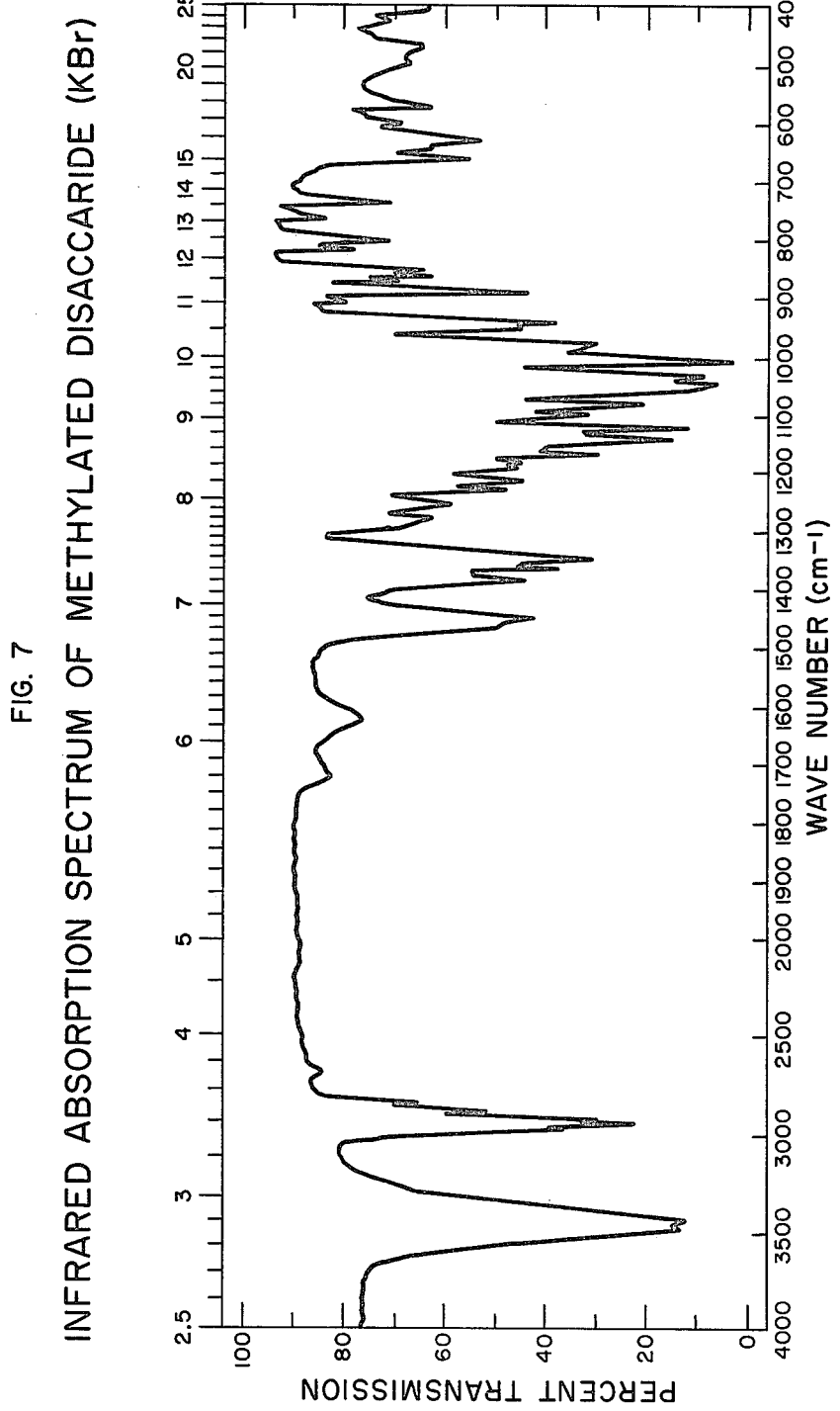
FIG. 7 is the infrared absorption spectrum of the methylated disaccharide.
Figure 8:
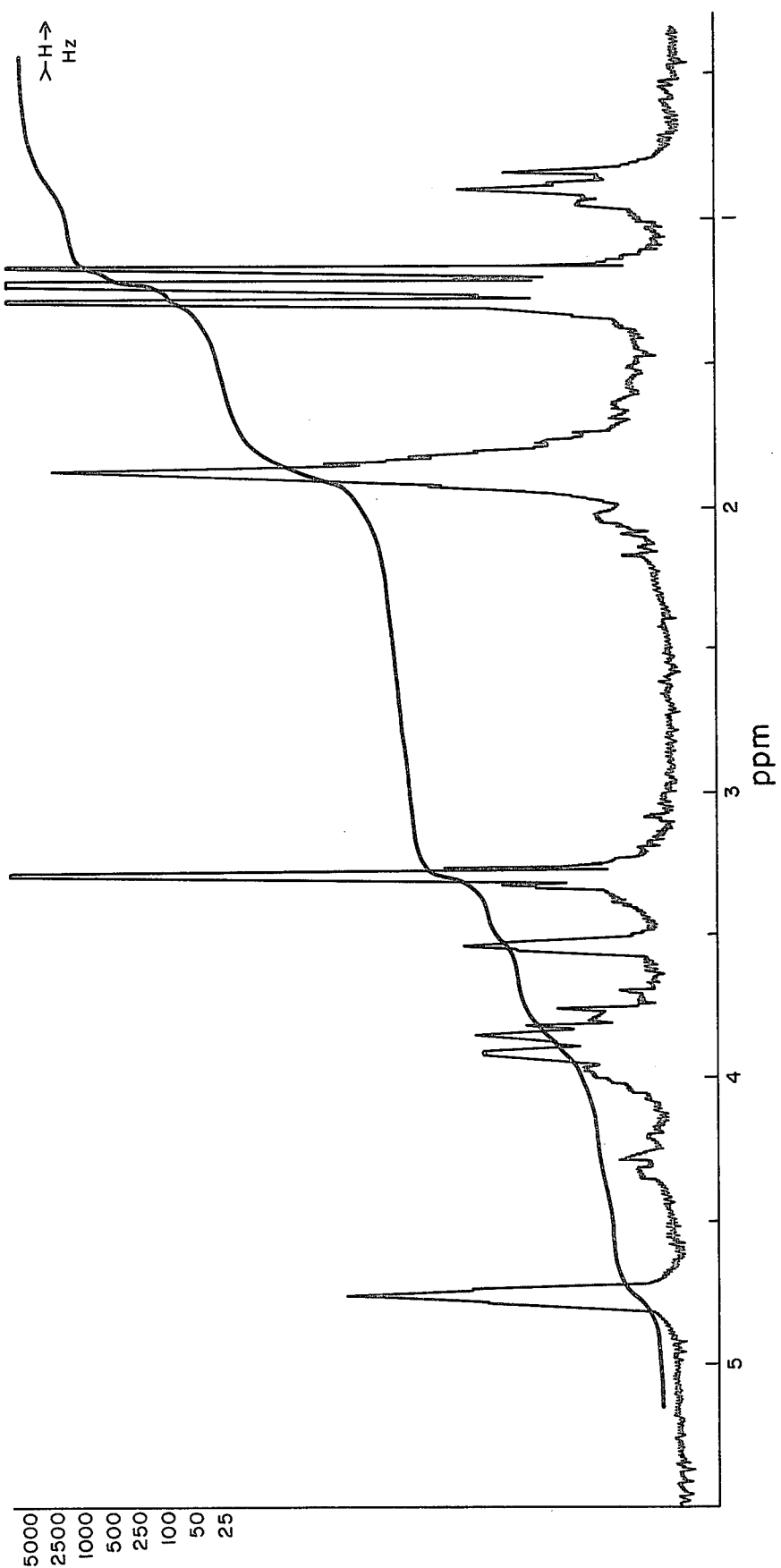
FIG. 8 shows the NMR spectrum of the methylated disaccharide.

Absorption spectra in the ultraviolet and visible ranges of the methylated disaccharide showed end absorption, and its infrared absorption and NMR spectra are shown in FIGS. 7 and 8, respectively. From the results analyzed above, the structure of the methyl disaccharide was determined to be

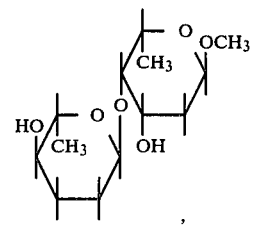

Methyl disaccharides obtained from MA 144-M$_1$ and MA 144-M$_2$ were identical to each other in their physicochemical properties.

On the methanolysis of MA 144-M$_1$ and MA 144-M$_2$, 1-deoxy-pyrromycin and pyrromycin were also demonstrated respectively on the basis of elementary analysis, absorption spectra of the infrared, ultraviolet and visible ranges, NMR spectrum, melting point, and the Rf values on silicic acid thin-layer.

From the results mentioned above, the structures of MA 144-M$_1$ and MA 144-M$_2$ in the present invention were determined to be as follows:

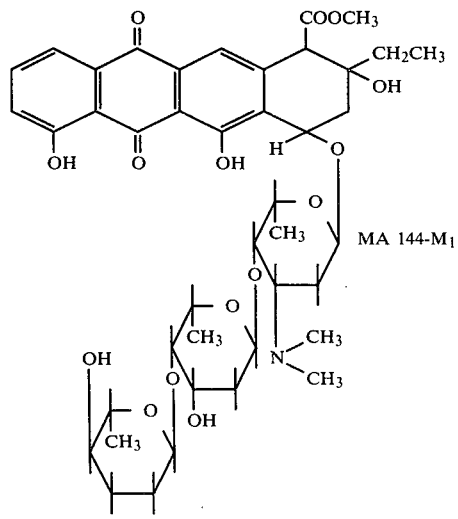

-continued

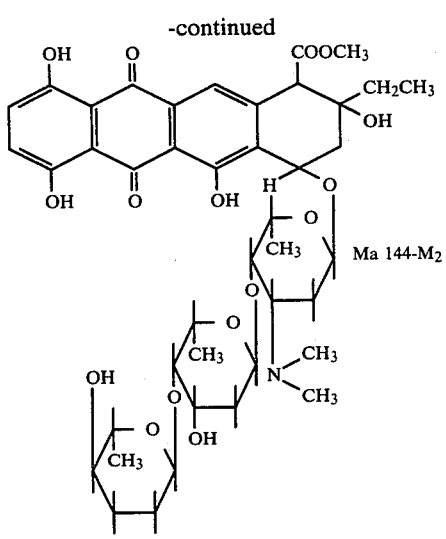

Ma 144-M₂

While a number of anthracycline glycoside antibiotics having aklavinone and ε-pyrromycinone aglycone moieties are known in the art, the compounds MA 144-M₁ and MA 144-M₂ are clearly different from any of them in such characteristics as molecular formula, degradation products on acid hydrolysis, ultraviolet, visible, infrared and NMR absorption spectra and the like, as described above. As mentioned above, MA 144-M₁ and MA 144-M₂ differ from their starting materials, aclacinomycin A and cinerubin A, in their terminal sugar. (References: 1. The Journal of Antibiotics 28 No. 10: 830–834 (1975). 2. Antimicrobial Agents and Chemotherapy: 68–77 (1970)).

Amicetose, which is the terminal sugar of the present compounds, has been identified only in the antibiotic, amicetin. (Reference: J. Am. Chem. Soc. 86: 3592–3594 (1964)). Among rhodomycin-type antibiotics, there is an antibiotic having a similar sugar moiety, rhodosamine-2-deoxyfucose-rhodinose, but it is clearly differentiated from MA 144-M₁ and MA 144-M₂ in its aglycone and terminal sugar. (Reference: Pharmazie 27: 782–789 (1972)).

Thus it is verified that MA 144-M₁ and MA 144-M₂ are new substances.

In order to further clarify the properties of MA 144-M₁ and MA 144-M₂, Rf values on silicic acid thin-layer using various solvent systems are shown below:

| Solvent system | Rf values | |
|---|---|---|
| | MA 144-M₁ | MA 144-M₂ |
| (1) chloroform : methanol = 10:1 | 0.45 | 0.45 |
| (2) chloroform : methanol = 20:1 | 0.11 | 0.11 |
| (3) acetone | 0.38 | 0.28 |
| (4) ethyl acetate | 0.024 | 0.024 |

Biological activities of MA 144-M₁ and MA 144-M₂ are as follows:

(1) MA 144-M₁ and MA 144-M₂ have antimicrobial activity against various kinds of microorganisms. The minimum inhibitory concentration of the present compounds determined by the broth dilution method is shown in Table 3.

Table 3

Minimum inhibitory concentration (MIC, μg./ml.) of MA 144-M₁ and MA 144-M₂

| Test organism | | MA 144-M₁ | MA 144-M₂ |
|---|---|---|---|
| Staph. aureus | FDA 209P | 3.1 | 0.78 |
| Staph. aureus | Smith | 0.2 | 0.1 |
| Bac. subtilis | ATCC 6633 | 0.4 | 0.05 |
| Bac. cereus | ATCC 9634 | 0.78 | 0.05 |
| Bac. megaterium | NRRL B-938 | 3.1 | 0.78 |
| Sarcina lutea | ATCC 341 | 0.05 | 0.05 |
| Mic. flavus | | 0.2 | 0.2 |
| Cory. bovis | | 0.4 | 0.1 |
| Ps. fluorescens | NIH JB-254 | >100 | >100 |
| Proteus morganii | (the Institute for Infectious Diseases) | >100 | >100 |
| Mycobact. smegmatis | ATCC 607 | 2.5 | 1.25 |
| Strept. pyogenes | NY 5 | 1.25 | 0.63 |
| Can. albicans | IAM 4905 | 100 | 50 |
| Can. tropicalis | IAM 4942 | >100 | 100 |

As stated above, MA 144-M₁ and MA 144-M₂ show antimicrobial activity against gram-positive bacteria, and thus they are therapeutically useful for diphtheria, tuberculosis, pneumonia, tetanus, infectious diseases caused by Staphylococcus and Streptococcus, etc.

(2) MA 144-M₁ and MA 144-M₂ also show a marked antitumor activity with low toxicity and are demonstrated to be effective for pharmaceutical use as anticancer agents.

(a) Therapeutic effectiveness on L1210-bearing mice

| Dosage (mg/kg/day) | Prolongation of the survival time (%) | |
|---|---|---|
| | MA 144-M₁ | MA 144-M₂ |
| 10 | 90 | — |
| 5 | 200 | 46 |
| 2.5 | 192 | 85 |
| 1.25 | 137 | 200 |
| 0.625 | 123 | 192 |
| 0.313 | 110 | 144 |
| 0.156 | 110 | 116 |

CDF₁-L1210. Drug was administered intraperitoneally from day 0 to day 10.

(b) Therapeutic effectiveness on P388-bearing mice

| Dosage (mg/kg/day) | Prolongation of the survival time (%) | |
|---|---|---|
| | MA 144-M₁ | MA 144-M₂ |
| 5 | 100 | 57 |
| 2.5 | 184 | 83 |
| 1.25 | 149 | 206 |
| 0.625 | 135 | 148 |
| 0.313 | 110 | 125 |

CDF₁-P388. Drug was administered intraperitoneally from day 1 to day 9.

(c) Therapeutic effectiveness on Sarcoma 180 solid tumor

| Dosage (mg/kg/day) | Weight of tumor(g) | | % Inhibition of tumor growth | |
|---|---|---|---|---|
| | MA 144-M₁ | MA 144-M₂ | M 144-M₁ | MA 144-M₂ |
| 5 | 0.38 | toxic | 77.4 | — |
| 2.5 | 0.65 | 0.28 | 61.3 | 83.3 |
| 1.25 | 0.81 | 0.39 | 51.9 | 76.8 |
| 0.6 | 0.78 | 0.90 | 53.7 | 46.5 |
| 0.3 | 1.25 | 1.41 | 25.5 | 16 |
| control | 1.68 | — | 0 | — | dd mice were inoculated with 2 × 10⁶ cells of Sarcoma 180, and drug was administered intraperitoneally from day 1 to day 10.

(3) Acute toxicity

The LD₅₀ of MA 144-M₁ and MA 144-M₂ is shown in the following table

| Animal | Route | LD$_{50}$ (mg/kg) MA 144-M$_1$ | MA 144-M$_2$ |
|---|---|---|---|
| Mouse | i.p. | 35 | 12.5 |
|  | i.v. | 30–35 | 12–20 |
| Rat | i.p. | 25–30 | 10–15 |
|  | i.v. | 25–30 | 10–15 |

(4) Cytotoxicity

MA 144-M$_1$ and MA 144-M$_2$ inhibited the growth of mammalian tumor cells in culture, especially at low concentration, and completely inhibited RNA synthesis. In this experiment, L1210 cells were inoculated in RPMI 1640 medium (Nissui, Roswell Park Memorial Institute 1640) containing 10% calf serum and cultivated at 37° C. for 3days in a CO$_2$ incubator, and MA 144-M$_1$, MA 144-M$_2$ and $^{14}$C-precursor were added at various concentrations. Effects on the synthesis of protein, RNA and DNA were indicated by the 50% inhibition concentration (μg./ml.) as shown in the following table. From the results, MA 144-M$_1$ and MA 144-M$_2$ inhibited markedly the growth of cultured L1210 cells and RNA synthesis at the low concentration. These results supported the therapeutic effectiveness on animal experimental tumors.

Effects of MA 144-M$_1$ and MA 144-M$_2$ on the growth and macromolecular synthesis in cultured L1210 cells

|  | ID$_{50}$ (μg./ml.) MA 144-M$_1$ | MA 144-M$_2$ |
|---|---|---|
| L1210 cells |  |  |
| Growth | 0.12 | 0.05 |
| DNA synthesis | 1.7 | 1.0 |
| RNA synthesis | 0.7 | 0.5 |
| Protein synthesis | *10 | — |

*% inhibition at the concentration of 10 μg./ml.)

As mentioned above, the compounds MA 144-M$_1$ and MA 144-M$_2$ possess marked inhibitory action against mammalian malignant tumors, especially on ascitic and solid tumors and leukemia. Thus, the compounds MA 144-M$_1$ or MA 144-M$_2$, their salts, or their complexes can be used as therapeutic agents against solid and ascitic-type malignant tumors.

The compounds in the present invention form non-toxic acid addition salts with a variety of organic and inorganic salt-forming reagents, and non-toxic complexes with nucleic acids. Thus, acid addition salts formed with such pharmaceutically acceptable organic or inorganic acids as sulfuric, phosphoric, hydrochloric, acetic, propionic, oleic, palmitic, citric, succinic, tartaric, glutamic, pantotheic, etc. can be employed in the same manner as the MA 144 compounds per se. These salts are formed, isolated, purified and formulated by the methods generally employed in salt formation for antibiotics. For example, the said chosen antibiotic and the intended acid are dissolved separately in an appropriate solvent which has a low solubility for salts, e.g., ethyl ether and acetone or their mixture, and then are mixed. The solution is concentrated if necessary and cooled, yielding the crystals of the said acid addition salt which are collected and dried to give a crystal-line powder. The resulting salts exhibit higher solubility in water than the corresponding antibiotics and are preferably used in a therapeutic application. In applying the antibiotics according to the present invention, a non-toxic complex such as a DNA complex is also used therapeutically. In this case DNA extracted from animals and microorganisms such as calf thymus, Hela cells, human and animal embryonic cells, yeasts, etc. can be used. Preparation of DNA-MA 144 complexes can be carried out by methods described in the literature for preparing DNA complexes of other anthracycline antibiotics such as adriamycin, daunorubicin, etc. [see, for example, Nature, New Biol. 239: 110 (1973) and Europ. J. Cancer 10:399 (1974)]. For purposes of this invention, the compounds in the free base form are equivalent to their non-toxic acid addition salts and complexes.

According to another aspect of this invention, a method is provided for therapeutically treating a mammalian host affected by leukemia, which comprises administering to said animal a leukemia-inhibiting dose of MA 144-M$_1$, MA 144-M$_2$ or a mixture thereof.

According to another aspect of this invention, a further pharmaceutical composition is provided comprising MA 144-M$_1$ or MA 144-M$_2$ or a mixture thereof in an amount sufficient to reduce the affection by leukemia in vivo, the MA 144-M$_1$, MA 144-M$_2$ or both substances being combined with an inert pharmaceutically acceptable carrier or diluent. It will be appreciated that the actual preferred amounts of the MA 144 substance used will vary according to the particular compound being used, the particular composition formulated, the mode of application and the particular situs and organism being treated. Many factors that modify the action of the drug will be taken into account by those skilled in the art, for example, age, body weight, sex, diet, time of administration, route of administration, rate of excretion, drug combinations, reaction sensitivities and severity of the disease. Optimal application rates for a given set of conditions can be ascertained by those skilled in the art using conventional dosage determination tests in view of the above guidelines.

When injected parenterally, MA 144-M$_1$ or MA 144-M$_2$, its salts or its complexes, is dissolved in distilled water for injection or physiological saline, and injected intraperitoneally, intravenously, subcutaneously or locally into the host animal. The dosage amount and injection route must take into consideration the results of animal experiments, the condition of patients and test animals, age, body weight, sex, sensitivity, injection schedule, injection period and combination with other drugs. Administration can be carried out continuously or periodically within the maximum tolerated dose.

The following examples are provided for illustrative purposes only and are not intended to limit the scope of the invention.

EXAMPLE 1

A mixture of the livers isolated from 10 Wister rats (300 g., ♂) and 10 volumes of 10 mM Tris buffer (pH 7.8) containing 10 mM magnesium chloride and 0.25 M sucrose was homogenized by a Teflon homogenizer and centrifuged at 10,000 rpm for 20 min. The supernatant (400 ml.) obtained was mixed with 50 ml. of 5 mg./ml. cinerubin A and 50 ml. of 6 mg./ml. NADP, distributed 50 ml. each in 500 ml.-flasks, and incubated at 40° C. for 1 hr. on a rotary shaker. Reaction was stopped by the addition of two volumes of cold chloroform-methanol (1:1) mixture. This solution was mixed well and separated from the chloroform layer, and the remaining active fraction in the aqueous layer was re-extracted with an equal volume of chloroform.

Both chloroform layers were combined, concentrated under reduced pressure, applied onto silicic acid thin-layer plates and developed with chloroform-methanol (10:1) mixture for preparation. After chromatography, the band corresponding to MA 144-$M_2$ was scratched off and MA 144-$M_2$ was extracted with methanol, concentrated under reduced pressure and crystalized from a chloroform-n-hexane mixture. There was obtained 51.3 mg. of red needle crystals of MA 144-$M_2$.

EXAMPLE 2

Using mouse liver homogenates as an enzyme source, 100 mg. of aclacinomycin A was treated according to the same procedure as described in Example 1 (coenzyme used was NADP), and 48.5 mg. of MA 144-$M_1$ was obtained as a yellow powder.

EXAMPLE 3

Using fresh rabbit liver slices as an enzyme source, 200 mg. of the mixed substrate including 35.5 mg. cinerubin A and 112.5 mg. aclacinomycin A was incubated with liver slices and coenzyme NADP in 1000 ml. of a magnesium-sucrose-Tris solution (pH 7.8) as described in Example 1.

The reaction mixture was extracted with chloroform, and 20 ml. of 1% $CuSO_4.5H_2O$ was added to the chloroform layer (100 ml.). After the solution was shaken vigorously, $10^{-3}$ M EDTA solution was added to the chloroform layer separated from the aqueous layer and shaken vigorously, and the chloroform layer was then washed by shaking twice with a small amount of water. The chloroform extract was concentrated, and 51 mg. of MA 144-$M_1$ yellow powder was obtained by the addition of n-hexane. The initial aqueous layer containing the precipitation of $Cu^{++}$-chelated MA 144-$M_2$ complex was centrifuged, and the precipitate was washed with acetone, dissolved in 10 ml. of 0.1 N HCl, and extracted with an equal volume of ethyl acetate. The extract was washed twice with NaCl-saturated water, washed with water again, and concentrated under reduced pressure. By the addition of n-hexane to the concentrate, 10.5 mg. of MA 144-$M_2$ was obtained as a red powder.

EXAMPLE 4

One gram of aclacinomycin A was dissolved in 40 ml. of ethyl acetate, mixed with 40 ml. water containing 100 mg. of sodium borohydride, and shaken vigorously for 20 min. at room temperature in a separatory funnel. The reaction mixture was allowed to stand and separate from the ethyl acetate layer, and the extract was washed with the NaCl-saturated solution containing $10^{-5}$ M EDTA, washed twice with water, and then concentrated after dehydration with anhydrous sodium sulfate. After silicic acid column chromatography (3×20 cm.) using toluene-methanol mixture (100:3), active fractions containing MA 144-$M_1$ were pooled, concentrated, and added to n-hexane. The resultant yellow precipitate of MA 144-$M_1$ weighed 450 mg.

EXAMPLE 5

Cinerubin A (2 g.) was dissolved in 80 ml. of ethyl acetate-chloroform-methanol mixture (10:1:1), mixed with 80 ml. water containing 200 mg. of sodium borohydride, and shaken vigorously for 20 min. at room temperature in a separatory funnel. Further purification was carried out according to Example 4 and 760 mg. of MA 144-$M_2$ was obtained from ethyl acetate-n-hexane as red needle crystals.

EXAMPLE 6

A nutrient medium having the following composition was prepared:

| Potato starch | 2% w/v |
|---|---|
| Glucose | 2 |
| "Meat" (Trademark of Soybean Powder) | 2.5 |
| $KH_2PO_4$ | 0.1 |
| $K_2HPO_4$ | 0.1 |
| $MgSO_4 . 7H_2O$ | 0.1 |
| NaCl | 0.3 |
| $MnCl_2 . 4H_2O$ | 0.000s |
| $FeSO_4 . 7H_2O$ | 0.0005 |
| Silicone | 0.005 (pH 7.2) |

Fifty ml. of this medium was sterilized at 120° C. for 15 min. in a 500 ml.-flask which was inoculated with one ml. of frozen culture of Streptomyces galilaeus MA 144-$M_1$ (FERM P-2455) and incubated at 30° C. for 48 hours on a rotary shaker. Ten liters of the previously sterilized medium in a 20 liter stainless steel jar fermentor were aseptically inoculated with 200 ml. of the above seed culture. Fermentation was carried out at 30° C. for 18 hrs. with agitation (300 rpm) and aeration (5 l/min.). Then, 10 liters of this culture were transfered to 600 liters of the previously sterilized medium in a 1 Kl-stainless steel tank as the second seed, and cultured at 30° C. for 48 hrs. with agitation (180 rpm) and aeration (200 l/min.).

The cultured broth obtained (570 liters) was adjusted to pH 5.0 with sulfuric acid and filtered with diatomaceous earth. The resulting filtered cake (54 kg.) was suspended in 7 liters of acetone and filtered after stirring for 3 hrs. The residue was re-extracted with 85 l of acetone. Both extracts were concentrated to 40 liters under reduced pressure, added to 25 liters of ethyl acetate, and stirred. After separating the ethyl acetate layer and concentrating to 1 liter under reduced pressure, crude aclacinomycin A mixture was precipitated by addition of n-hexane to the concentrate, and then 16 grams of orange yellow powder were obtained after washing twice with a n-hexane-ethyl acetate mixture (50:1).

This crude powder was dissolved in 200 ml. of ethyl acetate, applied onto a column filled with 700 grams of Column-Lite (Trademark of Fuji Chemical Co. for silicic acid), and eluted with an ethyl acetate-methanol mixture (1:1). The yellow eluate was concentrated to dryness under reduced pressure. The crude aclacinomycin powder obtained (12 g.) was dissolved in 100 ml. of chloroform, shaken with 50 ml. of $10^{-3}$ M EDTA-0.01 M phosphate buffer (pH 6.8) to remove residual metal ions, and the chloroform layer was washed twice with water, dried with anhydrous sodium sulfate and then concentrated to dryness under reduced pressure. There was obtained 11 grams of yellow powder containing aclacinomycin A.

This powder was dissolved in a small amount of toluene, applied to a silicic acid column (4×40 cm.), and eluted. Aclacinomycin A, B and other impurities were eluted with 2% (v/v) methanol-containing toluene and then the MA 144-$M_1$ fraction was eluted with 3% methanol-containing toluene and concentrated to dryness to give 10.5 mg. of MA 144-$M_1$ as a yellow powder.

The above-mentioned Column-Lite column after elution of the yellow fractions was treated with $10^{-3}$ M EDTA-containing 30% (v/v) methanol mixture, and the resulting red eluate was evaporated to dryness to give 5.0 grams of red powder containing cinerubin A. This red powder was treated with EDTA and chromatographed by a silicic acid acid column as described for MA 144-$M_1$. There was obtained 6.2 mg. of MA 144-$M_2$ as a red powder.

We claim:

1. A process for producing the antibiotic MA 144-$M_1$ which comprises incubating aclacinomycin A at a temperature in the range of 20° C. to 42° C. and at a pH from 5.5 to 10.5 in a medium containing an enzyme system capable of converting aclacinomycin A to MA 144-$M_1$ and a coenzyme, said enzyme system being obtained from mammalian tissue or from a MA 144 producing streptomyces and said coenzyme being nicotinamide adenine dinucleotide phosphate or the reduced form of nicotinamide adenine dinucleotide phosphate, and thereafter recovering the MA 144-$M_1$ from the reaction mixture in substantially purified form.

2. The process according to claim 1 in which said converting enzyme system is a member selected from the group consisting of mammalian organs, tissue slices, tissue homogenates, dried preparations thereof, partially purified enzymes thereof and immobilized enzymes thereof.

3. The process according to claim 1 in which said converting enzyme system is a member selected from the group consisting of cultured broth of the MA 144 producing streptomyces, cell suspension obtained therefrom, dried cell obtained therefrom, cell homogenate obtained therefrom, supernatant solution obtained therefrom, partially purified enzyme obtained therefrom and immobilized enzyme obtained therefrom.

4. The process according to claim 3 in which the MA 144 producing streptomyces is a member selected from the group consisting of *Streptomyces galiaeus* MA 144-$M_1$ ATCC 31133 (FERM P-2455), Streptomyces sp. ME 505-HE1 ATCC 31273 (FERM P-3667), *S. galiaeus* ATCC 14969, *S. cinereoruber* ATCC 19740, *S. niveoruber* ATCC 14971, *S. antibioticus* ATCC 8633, *S. purpurascens* ATCC 25489 and mutants thereof.

5. The process according to claim 1 in which the cultured broth obtained from an aclacinomycin A producing streptomyces is used as the source of aclacinomycin A.

6. A process for producing the antibiotic MA 144-$M_2$ which comprises incubating cinerubin A at a temperature in the range of 20° C. to 42° C. and at a pH from 5.5 to 10.5 in a medium containing an enzyme system capable of converting cinerubin A to MA 144-$M_2$ and a coenzyme, said enzyme system being obtained from mammalian tissue or from a MA 144 producing streptomyces and said coenzyme being nicotinamide adenine dinucleotide phosphate or the reduced form of nicotinamide adenine dinucleotide phosphate, and thereafter recovering the MA 144-$M_2$ from the reaction mixture in substantially purified form.

7. The process according to claim 6 in which said converting system is a member selected from the group consisting of mammalian organs, tissue slices, tissue homogenates, dried preparations thereof, partially purified enzymes thereof and immobilized enzymes thereof.

8. The process according to claim 6 in which said converting enzyme system is a member selected from the group consisting of cultured broth of the MA 144 producing streptomyces, cell suspension obtained therefrom, dried cell obtained therefrom, cell homogenate obtained therefrom, partially purified enzyme obtained therefrom and immobilized enzyme obtained therefrom.

9. The process according to claim 6 in which the MA 144 producing streptomyces is a member selected from the group consisting of *Streptomyces galiaeus* MA 144-$M_1$ ATCC 31133 (FERM P-2455), Streptomyces sp. ME 505-HE1 ATCC 31273 (FERM P-3667), *S. galiaeus* ATCC 14969, *S. cinereoruber* ATCC 19740, *S. niveoruber* ATCC 14971, *S. antibioticus* ATCC 8663, *S. purpurascens* ATCC 25489 and mutants thereof.

10. The process according to claim 6 in which the cultivated broth obtained from a cinerubin A producing streptomyces is used as the source of cinerubin A.

* * * * *